US006372794B1

(12) United States Patent
Nimni

(10) Patent No.: US 6,372,794 B1
(45) Date of Patent: Apr. 16, 2002

(54) METHOD FOR ALLEVIATING ARTHRITIS IN MAMMALS

(76) Inventor: Marcel E. Nimni, 2800 Nelson Way, Apt. 908, Santa Monica, CA (US) 90405

( * ) Notice: Subject to any disclaimer, the term of this patent is extended or adjusted under 35 U.S.C. 154(b) by 0 days.

(21) Appl. No.: 09/383,845

(22) Filed: Aug. 26, 1999

(51) Int. Cl.[7] ..................... A61K 38/00; A61K 31/185; A61K 31/70; A61K 31/715; C09H 1/00

(52) U.S. Cl. .......................... 514/578; 514/62; 514/54; 514/12; 514/801; 530/362

(58) Field of Search .................. 514/801, 62, 578; 530/362

(56) References Cited

U.S. PATENT DOCUMENTS

| 4,444,752 A | 4/1984 | Prudden ...................... 424/95 |
| 4,601,896 A | 7/1986 | Nugent ......................... 424/36 |
| 4,704,273 A | 11/1987 | McMichael ................... 424/85 |
| 5,075,112 A | 12/1991 | Lane ........................... 424/434 |
| 5,399,347 A | 3/1995 | Trentham et al. |
| 5,529,786 A | 6/1996 | Moore |
| 5,840,715 A | * 11/1998 | Florio ........................... 514/62 |
| 5,856,446 A | * 1/1999 | Weiner et al. ............... 530/356 |

OTHER PUBLICATIONS

"Harvard Scientists Find Nutrient Critical To Joint Problems", Bone And Joint Health, © 1998 vol. 4/No. 8.
"Administración de Colágeno II como Tratamiento de la Artritis Reumatoidea" vol. XV—No. 3, 1998 published in Alergia E InmunologíClínica.
"Collagen–Induced Arthritis in Rats: Antigen–Specific Suppression of Arthritis and Immunity by Intravenously Injected Native Type II Collagen"by Michael A. Cremer, et al., "The Journal of Immunology" © 1983 by The American Association of Immunologists.
"Cellular Immunity To The G1 Domain of Cartiglage Proteoglycan Aggrecan Is Enhanced In Patients With Rheumatoid Arthritis But Only After Removal Of Keratan Sulfate" by Alexei Guerassimov, et al.,Arthritis & Rheumatism, vol. 41, No. 6, Jun. 1998, pp 1019–1025 © 1998, American College of Rheumatology.
"Immunologic Suppression after oral Administrationof Antigen" in Cellular Immunology 86, 46–52 (1984).
"Oral Type II Collagen Treatment In Early Rheumatoid Arthritis" in Arthritis & Rheumatism, vol. 39, No. 1, Jan. 1996, pp 41–51 © 1996, American College of Rheumatology.
"Immunosuppression caused by antigen feeding II. Suppressor T cells mask Peyer's patch B cell priming to orally administered antigen", © Verlag Chemie GmbH, D–6940 Weinheim, 1983, by Thomas Thornton MacDonald, Department of Microbiology, Jefferson Medical College, Philadelphia.
"Different strains of rats develop different clinical forms of adjuvant disease", by Valerie Y. Muir and D. C. Dumonde, "Annals of the Rheumatic Diseases," 1982, 41, 538–543, from the Department of Immunology, St. Thomas's Hospital Medical School, London SE1 7EH.
"Treatment of Rheumatoid Arthritis With Oral Type II Collagen: Results of a Multicenter, Double–Blind, Placebo–Controlled Trial", by Martha L. Barnett, et al., Arthritis Rheum, vol. 41(2), Feb. 1998, pp 290–297.
"Effects of Oral Administration of Type II Collagen on Rheumatoid Arthritis", by David E. Trentham, et al., Reprint Series, Sep. 24, 1993, vol. 261, pp. 1727–1730.
"Collagen–Induced And Adjuvant–Induced Arthritis In Rats" "Post–Immunization Treatment with Collagen to Suppress or Abrogate the Arthritic Response", by Kalindi Phadke, et al., Arthritis and Rheumatism, vol. 27, No. 7 (Jul. 1984).
"A Pilot Trial of Oral Type II Collagen in the Treatment of Juvenile Rheumatoid Arthritis" by Martha L. Barnett, et al., Arthritis and Rheumatism, vol. 39, No. 4, Apr. 1996, pp. 623–628.
"Properties of a Collagen Molecule Containing Three Identical Components Extracted from Bovine Articular Cartilage" by Elsa Strawich and Marcel E. Nimni, Biochemistry, vol. 10, No. 21, 1971, pp. 3905–3911.

* cited by examiner

*Primary Examiner*—Theodore J. Criares
(74) *Attorney, Agent, or Firm*—Oppenheimer Wolff & Donnelly LLP; Michael B. Farber

(57) ABSTRACT

A method for alleviating arthritis in mammals by the oral administration of a pharmaceutical composition compound of native Type II collagen in helical form and sulfated polysaccharides found in mammalian cartilage, the Type II collagen and sulfated polysaccharides being ionically bound.

10 Claims, No Drawings

METHOD FOR ALLEVIATING ARTHRITIS IN MAMMALS

FIELD OF THE INVENTION

The major constituents of cartilage are collagen and a variety of anionic high molecular weight carbohydrates (sulfated polysaccharides) associate with proteins in the form of proteoglycans. Both cartilage collagen and the cartilage specific carbohydrate moieties, more specifically the chondroitin sulfatate components of these carbohydrate fractions, are used with various degrees of success in treating patients afflicted with arthritis. The method of the present invention generates a mixture of these native molecules in concentrations and quality which reflect their proportions found in the native tissue. Ionic interactions between the collagen, which retains a fibrillar configuration, and the negatively charged sugars stabilizes the composition in the acid environment of the stomach and facilitates its dissociation in the alkaline environment of the small intestine. This has been found to be extremely effective in ameliorating symptoms and reversing changes associated with joint diseases in afflicted dogs and cats and appears to be equally effective in humans.

BACKGROUND OF THE INVENTION

Arthritis, particularly rheumatoid arthritis (RA), is a chronic, inflammatory disorder of unknown etiology, affecting approximately 1% of the world's population. Women are affected three to four times more often than men. Some populations are less affected (Asians and Nigerians), and others, such as certain Native American Indians, show a much higher incidence (5–6%).

In most patients symptoms begin as gradually increasing malaise and fatigue, likely to be accompanied by diffuse musculoskeletal pain. Joint involvement is appreciated as pain, tenderness, swelling, and redness. Symmetry is characteristic, most commonly involving the joints of the hands, wrists, elbows, and shoulders, but also involving the knees, ankles, and feet; virtually any diarthrodial joint can be affected.

Arthritis is associated with a decreased life span, in part because of the systemic nature of the disease and in part related to the toxicities of various treatments. The median life expectancy of persons with established arthritis is less than that of control populations. One study showed that median life expectancy was shortened by 7 years in males and 3 years in females.

Most patients exhibit a chronic fluctuating course of disease that, if left untreated, results in progressive joint destruction, deformity, disability, and premature death. RA results in more than 9 million physician visits and more than 250,000 hospitalizations per year in the USA. It frequently affects patients in their most productive years, and thus, disability results in major economic loss. There is no known cure for RA or means of preventing it. Optimal management requires early diagnosis and timely introduction of agents that reduce the probability of irreversible joint damage.

The initial drug treatment of RA usually involves the use of NSAIDs to reduce joint pain and swelling and improve function. If non-prescription drugs fail to help the patients, other drugs that require more careful monitoring are often used. All drugs used to treat RA may cause death, disability, and diseases, especially if the treatment continues in the setting of undetected toxicity. The incidence of toxicity may be reduced by pretreatment assessment of individual risk factors for toxicity and by careful patient and physician education about safe use of the drug. Patients must be alert to the sign and symptoms of toxicity that should prompt discontinuation of the drug and physician reassessment. Some drug toxicity may be discovered by appropriate laboratory monitoring before serious problems become clinically apparent.

In view of the hazards associated with the treatment of this disease, it is reasonable to expect that alternate, less potentially damaging approaches have been sought. Evidence suggests that dietary fish oil supplements may help alleviate symptoms of rheumatoid arthritis. The oil, obtained from cold-water fish, contains omega-3 polyunsaturated acids. Fish oil is known to prolong bleeding time and to inhibit platelet aggregation. These effects could be dangerous in patients taking other anticoagulants, including aspirin.

In 1993, a group of researchers in Boston (Trentham et al.) reported that a collagen preparation taken by mouth reduced inflammation in a small group of people with severe rheumatoid arthritis. These researchers used Type II collagen, a major component in joint cartilage. Animal studies by these and other investigators using a variety of animal models predicted these findings and preceded these studies in humans for many years.

Collagen is a protein that is a major component of all structural tissue in the body, including skin, bone, and joints. Type II collagen is the specific type of collagen found in cartilage and was first characterized in mammals by Strawich & Nhnni in 1971. Researchers believe that in rheumatoid arthritis, Type II collagen taken by mouth may turn off cells that are involved in causing inflammation or may prevent the immune system into responding to the inflammation.

Cartilage derived collagen (Type II) obtained from the breastbone extension of healthy chickens, is consumed in billions of households, yet cooking by denaturing the proteins, may inactivate the active substance. It still remains to be learned whether chicken soup, famous for its "therapeutic properties" may contain some biologically active derivatives. Even if this were the case, it would be difficult to standardize its activity and provide on a regular basis, pre-established amounts of active collagen by this route, which is essential for inducing immune tolerance orally to an antigenic substance.

Another cartilage containing substance, very different from collagen and the protein core of proteoglycans, and which is not a protein, includes a series of sulfated polysaccharides of which the chondroitin sulfate is amongst the best known species. These sulfated sugars have also been proposed to treat a variety of joint problems, particularly a non-inflammatory age related syndrome known as osteoarthritis or degenerative joint disease (DJD). Although distinct in nature rheumatoid arthritis and DJD usually have sufficient commonality to respond to similar treatment.

SUMMARY OF THE INVENTION

We have found that to alleviate arthritis it is important to orally administer native Type II collagen in helical form from mammalian cartilage ionically bound with sulfated polysaccharides. It is preferred if the weight ratio of the collagen to the polysaccharide is approximately the same as found in cartilage(i.e. about 6 to 1). The weight ratio may vary from about 5:1 to 30:1 with the preferred range being about 5:1 to 20:1. This approach yields a proper balance of the protein and carbohydrate components which are used to yield the building blocks for new material by the cartilage cells (particularly the sulfate moiety) and at the same time provide Type II collagen which decreases the severity of the inflammatory response.

As noted above, in my invention it is important to have the Type II collagen in helical form and ionically bound to the sulfated polysaccharides. This makes the composition of my invention very difficult to degrade by the enzymes in the gastrointestinal track. This allows my pharmaceutical compositions to have a slow "timed release" which is presently believed to, at least in part, account for the surprising results achieved in alleviating arthritis. It is also believed that having the Type II collagen in a fibrillar form is of benefit to achieve the slow "time release".

It is generally preferred that the sulfated polysaccharides include chondroitin sulfate and even more preferred if more than 50%, by weight, (e.g. more than 75% by weight) of the polysaccharides be chondroitin sulfate. It is also preferred if the sulfated polysaccharides include keratan sulfate, as e.g. 5% or more by weight (up to about 10%). Thus, preferably, the total amount of sulfated keratan in my invention will be between about 2.5% by weight and 7.5% by weight.

The method of my invention allows me to remove the collagen extensions located on the surface of the collagen fiber, which only involves around 10% to 20% of the molecules, while leaving intact the peptides located inside the fiber. The proteoglycans are only partially degraded under these conditions, since those that are ionically bound to the surface of collagen as a result of the acidic pH of the environment remain protected against this limited proteolysis.

DETAILED DESCRIPTION OF THE PREFERRED EMBODIMENTS

Type II collagen in mammalian cartilage (bovine articular cartilage) was first described and characterized in our laboratories in 1971 (Strawich and Nimni, Biochemistry). Our work and the subsequent work of many others relied on proteolytic enzymes to break down the non-helical polypeptide extensions which allow the native molecules assembled into a fibrillar network to form crosslinks. Degrading these extensions, which only account for a small proportion of the mass of the collagen molecule (around 1%) releases these molecules, which are subsequently solubilized by slightly acidic or cold balanced electrolyte solutions.

The proteolytic enzymes used, such as pepsin or papain, degrade in addition the protein backbone that hold the sulfated polysaccharides in place, chondroitin sulfate being an important species of such sulfated polysaccharides. Under these conditions, the sulfated polysaccharides are also released from their proteoglycan assembly and appear in solution. At neutral pH, these two species, the protein collagen and the sulfated polysaccharides, including chondroitin sulfate, are separated, and together with the degradation products of the protein core that holds the sulfated polysaccharides in place are discarded.

This aggregate, or co-precipitate, retains in an electrostatically bound form the cartilage specific macromolecules namely collagen Type II and the chondroitin sulfate rich sulfated polysaccharide fractions. It should be emphasized that using the procedure described, at no time do the collagen molecules and the sulfated polysaccharide constituents dissociate and go into solution. Methods employed by others, on the other hand, dissociate these components, encourage them to enter into solution and then selectively separate them or isolate them.

Chick sternal cartilage, obtained fresh from farms which process chickens for human consumption, are immediately frozen to $-15°$ C. For processing they are cleaned of the perichondrium and the specimens cut into small pieces, and placed in a solution containing 0.5M acetic acid and 5% NaCl (w/vol) and pepsin 200 mg/100 ml. The temperature of this solution is maintained at $4-8°$ C. and the specimens are incubated for 12 hours. This extraction is repeated again for 12 hours and in each case the supernatants are discarded.

To remove the proteolytic enzyme and non-active peptide degradation fragments, the aggregate is extracted with the aid of several changes of excess volume of 0.5% acetic acid solution containing 5% NaCl. If necessary low speed centrifugation is used at this stage to separate any excess of supernatant. The resulting aggregate contains the collagen with ionically bound sulfated polysaccharide chains and proteoglycan remnants. This approach contrasts with that used previously by us and other workers in the field, which followed this latter step with solubilization of the aggregate in neutral salt isotonic solutions. This solubilizes the active components, while dissociating the collagen from sulfated polysaccharide. Salting out the collagen from this solution at neutral pH retains the sulfated polysaccharide in solution, and these are usually discarded in the process of purification of collagen. I believe that retaining the sulfated polysaccharide fragments, associated with the collagen, some of which contain associated proteoglycan core protein, contributes significantly to the enhanced clinical efficacy of the compositions of the present invention.

Once isolated, the collagen-sulfated polysaccharide composition is mixed with excipients and tableted for oral ingestion. It is resistant to enzymatic digestion until it reaches the intestinal tract where it is believed to be degraded into large fragments which are recognized by the Payer cells in the small intestine. It is this bioactive composition that I find superior to any other natural cartilage derived material tested for efficacy in the treatment of rheumatoid arthritis and joint diseases in dogs.

The precipitated aggregate, which contains the collagen Type II in a fibrillar form (which contains at least 50% by weight of the non-helical telopeptides) and the aggregated sulfated polysaccharides (rich in chondroitin sulfate) is frozen and disintegrated with the aid of a homogenizer. The resulting microfibrillar material is further pulverized in the presence of solid calcium carbonate after freeze drying. The resulted granular material is further diluted with excipients such as dextrose and corn starch which are known to stabilize the macromolecules aggregate and finally by sequential addition of excipients diluted to a concentration that will yield tablets containing $25\gamma g$ of collagen.

EXPERIMENTAL FINDINGS

A clinical-therapeutic study was performed in dogs and cats, affected with different joint pathologies. Animals were treated with the Collagen Type II sulfated polysaccharide (prepared as described herein), 90 $\gamma$ (0.09 mg) administered as tablets, one a day, in consecutive days for a total of 90 days. Thirty-eight dogs and 2 cats are included in this study, 20 of which had received previous treatment with other drugs without positive results. All animals treated showed clinical improvement. No collaterals adverse effects were observed.

The population studied consisted of 17 females and 23 males, all with varying degrees of joint involvement, 37% were younger than 7 years, 47% ranged between 7 and 10 years of age and the remaining 15% were older than 10 years. The severity of the disease was rated clinically and radiographically and scored between 4 (very severe disease) to 1 (mild disease). Pain and range of motion was evaluated using a similar scale.

TABLE 1

Pain intensity before and after receiving treatment for 90 days

| Pain Score | No. of Animals Before Treatment | No. of Animals After Treatment |
|---|---|---|
| 4 | 5 | 0 |
| 3 | 21 | 1 |
| 2 | 11 | 3 |
| 1 | 3 | 11 |
| 0 | 0 | 25 |

4 = Most Severe 0 = No Pain

TABLE 2

Range of motion before and after treatment

| Pain Score | No. of Animals Before Treatment | No. of Animals After Treatment |
|---|---|---|
| 4 | 6 | — |
| 3 | 19 | 1 |
| 2 | 10 | 3 |
| 1 | 5 | 11 |
| 0 | — | 25 |

4 = Most Restricted 0 = Normal

Subjective parameters improved accordingly during treatment. It appeared that the younger animals showed earlier and more significant rates of improvement. No patients at any time showed any sign of enhancement of the disease.

It should be indicated, that in contrast to most other studies in animals and humans, this population included pathologies associated with a variety of etiologies (osteoarthritis, rheumatoid arthritis, various joint displasias, herniated discs). The positive response seen in all cases suggests that the common inflammatory component associated with a variety of joint problems can be ameliorated by altering the degree of immune related pathologies responsible for cartilage destruction.

Collagen/sulfated polysaccharide ratio can be estimated by hydroxyproline and uronic acid analysis. In articular cartilage the ratios of collagen to sulfated polysaccharide acid is around 6:1. Our preparations using various modifications of the extraction procedure yielded materials with ratios which varied between 6:1 to 20:1. The one used in this study is 10:1.

Although the present invention has thus been described in detail with regard to the preferred embodiments, it should be apparent to those skilled in the art that various adaptations and modifications of the present invention may be accomplished without departing from the spirit and the scope of the invention. Accordingly, it is to be understood that the detailed description as set forth hereinabove is not intended to limit the breadth of the present invention, which should be inferred only from the following claims and their appropriately construed legal equivalents.

What is claimed is:

1. A method for alleviating arthritis in a mammal comprising the steps of:

providing a pharmaceutically effective amount of a composition consisting essentially of Type II collagen in its helical form ionically bonded to at least one sulfated polysaccharide in its aggregate form, wherein more than 50% by weight of the sulfated polysaccharide is chondroitin sulfate, the Type II collagen being substantially undissociated into monomer collagen molecules and substantially retaining its native quaternary structure; and administering said composition to said mammal.

2. A method according to claim 1 wherein the Type II collagen retains more than 50% by weight of its non-helical sequences.

3. A method according to claim 2 wherein the Type II collagen is fibrous.

4. A method according to claim 1 wherein the sulfated polysaccharides include chondroitin sulfate.

5. A method according to claim 4 wherein the sulfated polysaccharides include keratan sulfate.

6. A method according to claim 1 wherein between about 5 wt. percent and about 10 wt. percent of the sulfated polysaccharide is keratan sulfate.

7. A method according to claim 1 wherein the weight ratio of Type II collagen to polysaccharides is between about 5:1 to 30:1.

8. A method according to claim 3 wherein the weight ratio of Type II collagen to sulfated polysaccharides is between about 6:1 to 20:1.

9. A method according to claim 1 wherein the amount of said pharmaceutical composition orally administered to said animal is between about 0.05γ and 0.5 mg per kilogram of the weight of the mammal.

10. A method according to claim 1 wherein said mammal is human.

* * * * *